United States Patent [19]
Phillippi et al.

[11] Patent Number: 5,596,134
[45] Date of Patent: Jan. 21, 1997

[54] CONTINUOUS OXYGEN CONTENT MONITOR

[75] Inventors: R. Michael Phillippi, Highland; Tadeusz M. Drzewiecki, Rockville; Stephen A. Freimanis, Germantown, all of Md.

[73] Assignee: Defense Research Technologies, Inc., Rockville, Md.

[21] Appl. No.: 419,577

[22] Filed: Apr. 10, 1995

[51] Int. Cl.$^6$ .......................... G01N 27/46; G01N 27/26
[52] U.S. Cl. ................... 73/19.07; 73/19.01; 205/783.5; 205/785; 204/421
[58] Field of Search .................... 73/19.07, 19.01, 73/19.08, 19.10; 205/783.5, 784, 785, 784.5, 484.5; 204/421–429

[56] References Cited

U.S. PATENT DOCUMENTS

| | | | |
|---|---|---|---|
| 3,359,188 | 12/1967 | Fischer | 204/1 |
| 3,378,478 | 4/1968 | Kolodney et al. | 204/195 |
| 3,464,008 | 8/1969 | Meysson et al. | 73/19.07 |
| 3,619,381 | 11/1971 | Fitterer | 204/1 T |
| 3,652,427 | 3/1972 | Flood et al. | 204/1 T |
| 3,723,279 | 3/1973 | Fruehan et al. | 204/195 S |
| 3,752,753 | 8/1973 | Fitterer | 204/195 S |
| 3,773,641 | 11/1973 | Fitterer | 204/195 S |
| 3,791,954 | 2/1974 | Noda et al. | 204/195 S |
| 3,793,155 | 2/1974 | Flood et al. | 204/195 S |
| 3,864,232 | 2/1975 | Handman et al. | 204/195 S |
| 3,883,408 | 5/1975 | Kim et al. | 204/195 S |
| 4,105,507 | 8/1978 | Vonkrusenstierna et al. | 204/1 T |
| 4,170,534 | 10/1979 | Fitterer | 204/248 |
| 4,193,857 | 3/1980 | Bannister et al. | 204/195 S |
| 4,264,423 | 4/1981 | Negas et al. | 204/195 S |
| 4,313,799 | 2/1982 | Perkins | 204/1 T |
| 4,356,065 | 10/1982 | Dietz | 204/1 T |
| 4,407,704 | 10/1983 | Mase et al. | 204/1 T |
| 4,505,783 | 3/1985 | Mase et al. | 204/1 T |
| 4,627,892 | 12/1986 | Worrell et al. | 204/1 T |
| 4,721,533 | 1/1988 | Phillippi et al. | 136/234 |
| 4,721,534 | 1/1988 | Phillippi et al. | 136/234 |
| 4,784,728 | 11/1988 | Capone | 204/1 T |
| 4,786,374 | 11/1988 | Worrell et al. | 204/1 T |
| 5,007,988 | 4/1991 | Archer et al. | 204/153.18 |
| 5,071,528 | 12/1991 | Baucke et al. | 204/153.18 |
| 5,112,456 | 5/1992 | Worrell et al. | 204/153.18 |
| 5,352,344 | 10/1994 | Göhring et al. | 204/153.18 |
| 5,413,683 | 5/1995 | Murase et al. | 204/183.16 |
| 5,480,523 | 1/1996 | Cocker et al. | 204/153.18 |

OTHER PUBLICATIONS

DRT Technical Report TR–93–1, "Development of an Oxygen Sensor for Continuous Measurement in Molten Steel" by R. Michael Phillippi and Tadeusz M. Drzewiecki 43 pages

American Scientist, vol. 80 "Modern Steelmaking" by Nobuo Ohashi pp. 540–555.

*Primary Examiner*—Hezron E. Williams
*Assistant Examiner*—J. David Wiggins

[57] ABSTRACT

A continuous oxygen content monitor has a reference electrode embedded in a powdered chrome-chrome-oxide mixture and a counter electrode embedded in an elongate alumina-graphite sleeve which acts as the probe support body. Two hallow and spacer ablative steel domes encase the reference electrode and an intermediate air gap spacing and provide insulation to prevent thermal shock from damaging the monitor during insertion into the metal melt. A circuit provides counter emf across the sensing electrodes to prevent ion depletion of the reference material.

27 Claims, 6 Drawing Sheets

OUTPUT $V_B \approx V_{O_2}$

CONTINUOUS OXYGEN CONTENT MONITOR

BACKGROUND OF THE INVENTION

1. Technical Field

The present invention pertains to the measurement of the oxygen content of high temperature liquids and more particularly to an improved method and apparatus for the continuous monitoring of oxygen in molten metal.

2. Discussion of the Prior Art

Quality standards of modern manufacturing require steel having extremely low concentrations of contaminants such as sulfur and oxygen, typically a few parts per million. Non-metallic inclusions, particularly $Al_2O_3$, formed in the liquid steel are a direct consequence of excess oxygen and ultimately appear as surface defects during the rolling and finishing operations. These surface defects are responsible for a significant portion of costly and disruptive rejected or downgraded steel.

A major goal of modern steel makers is improved precision and control over the chemical properties of molten steel. Continuous real-time monitoring of these properties, especially the oxygen content, throughout the molten phase of steel making would be ideal, but has been heretofore unavailable.

Oxygen content (fugacity) sensing in liquid steel is currently performed using a disposable electrolytic zirconia galvanic cell. In general, the expendable oxygen content sensor (more commonly known as a throwaway or disposable oxygen sensor) is constructed of a solid state electrolytic material. Typically oxygen sensors consist of a ceramic solid state electrolyte (>99 percent oxygen ion conductivity) such as zirconia doped with calcia, magnesia or yttria (CaO, MgO or $Y_2O_3$). The sensor ceramics are fabricated as closed end tubes or as thin, dense discs. The opposed surfaces are metallized (e.g. with platinum, gold, silver, etc. ) and the open circuit emf across the metal leadouts provides a measure of oxygen content according to the now well known fugacity (Nernst) equation:

$$E(\text{millivolts})=0.0496T(°K.)\log [P_{o2}(\text{unknown})/P_{o2}(\text{reference})]$$

where $P_{o2}$ is the partial pressure (fugacity) of oxygen and $T(°K.)$ is the absolute temperature in degrees Kelvin. Temperature is measured independently, typically by a thermocouple positioned adjacent the sensing portion of the cell either internally or externally. A reference material of known oxygen content can be impressed on one of the surfaces of the sensor disc and the partial pressure of the unknown material is on the other side.

In the case of the disposable measurement device used in liquid steel, a closed-ended zirconia tube is used with a solid reference material of chrome/chrome-oxide packed into the tube interior.

Theoretically nothing has precluded the use of a zirconia-based sensor for continuous oxygen content measurement, but finding practical solutions to several difficult technical problems has posed obstacles. The first such obstacle, the need for simultaneous and continuous temperature measurement, has recently been overcome by the development of ruggedized protective sheath materials and configurations for thermocouples capable of continuous measurement of molten steel processes at temperatures in excess of 3000° F. even in the presence of aggressive slags. This work is exemplified in U.S. Pat. No. 4,721,534 (Phillippi) and No. 4,721,533 (Phillippi et al). Unsolved, however, have been the problems of the susceptibility of zirconia to thermal shock in all but very small tubes and discs and, especially, the eventual depletion (or aggregation) of oxygen ions in the reference material, typically $Cr—Cr_2O_3$, over long and continuous periods of operation in low concentration environments (<16 ppm).

In the 1970's efforts were made to develop improved solid electrolyte-based sensors, especially oxygen sensors, for metal melts. It was hoped that stabilization of the electrochemical material and improved physical processing methods for the sensor fabrication would overcome the physical instability and tendency toward thermal fracture of previous sensors. The quartz tube that contained a thin electrolyte disc in one end was discarded and replaced by a tube formed from the electrolyte material itself. Partially stabilized zirconia, $ZrO_2$ with about 3 wt % of MgO, was formed into a tubular shape, compacted, and sintered to increase density. The resulting sintered electrolyte material comprises two phases, cubic and tetragonal, and has improved mechanical strength and resistance to thermal shock. The tube can be filled with a solid reference electrode material together with thermocouple and electrical connection scheme as desired, but while this two-phased electrolyte tube can be used as an oxygen sensor in metallurgical melts and is widely used for this purpose today, such devices are still extremely short-lived, being capable of one ten second measurement in actual steel mill environments.

Although the oxygen partial pressure of $Cr—Cr_2O_3$ reference material is well characterized as a function of temperature and has been used for over a decade in disposable short-lived zirconia-based oxygen sensors, the ionic transport of oxygen proceeds from the cell interior to the liquid steel and continuous operation at low oxygen concentrations depletes the available oxygen supply by reducing the chrome oxide to elemental chrome metal. Reference material oxygen depletion ultimately produces zero output voltage with the effect of an apparent, but clearly erroneous, increase in steel $O_2$ content.

Furthermore, if the $O_2$ levels are higher than approximately 16 ppm, the ion transport is from liquid steel to cell interior, and the conductive chrome metal constituent is eventually oxidized to a saturation point where electrical continuity may be lost and an open circuit can occur with resultant loss of signal altogether. During this process the cell interior can become "flooded" with oxygen ions, thereby increasing the oxygen reference partial pressure and can yield an apparent reduction of steel oxygen content.

The cumulative effect of $O_2$ ion saturation or depletion of the reference material eventually causes stalling of the ionic transport process and produces "emf values of zero."Misleading oxygen concentration readings then result when the oxygen partial pressure relationship as a function of temperature for $Cr—Cr_2O_3$ is substituted in the fugacity, or Nernst equation. Volume constraints prevent simply increasing the total amount of reference material to offset the time-dependent degradation. An alternative approach is to use an electrolyte material with a much higher resistance to ion transport, such as stabilized thoria. Consequently a diminished ion flow rate and increased useful life results, but with a potential loss of sensitivity and increased cost. Another solution to measurement degradation due to cumulative ion transport is to provide a continuous source of fixed oxygen partial pressure gas, for instance an argon and oxygen mixture, fed from an external source through a tube extending through the probe to the reference side of the sensor circuit. Although the cost of the premixed reference gas would be slight, the cost and complexity of the supply apparatus would be high.

SUMMARY OF THE INVENTION

Accordingly, it is a primary object of the present invention to overcome the above mentioned disadvantages of the prior art by providing a solid oxide electrolytic galvanic cell capable of being directly immersed into and making continuous measurements of dissolved oxygen in molten ferrous-bearing materials.

Another object of the present invention is to develop a zirconia-based oxygen sensor for use in a continuous caster tundish and ladle refining facilities.

Yet a further object of the present invention is to provide a method for fabricating and directly immersing a zirconia-based cell for continuous measurement of oxygen content in molten steel that will prevent thermal shock failure.

Still another object of the present invention is to incorporate a null-balancing negative feedback circuit into a continuous oxygen sensor to counterbalance ion transport and indefinitely extend the useful life of the reference partial pressure material.

It is yet further an object of the present invention to prevent any parasitic emf (thermocouple effects) resulting from the temperature difference between electrical leadouts.

The present invention is generally characterized as an oxygen sensor for continuous measurement in molten metal having an elongate aluminum-graphite sleeve with a first hollow dome of ablative material attached to the lower end. A stabilized zirconia hollow tube with an ablative domed lower end extending into the first ablative dome is disposed in the lower portion of the tube and sealed around the lower tube portion by a collar of suitable castable refractory. An insulating air gap exists between the first or outer hollow dome and the second or inner dome at the lower end of the zirconia tube. A molybdenum wire extends through the sleeve from a connector affixed to a flange at upper end of the sleeve to a molybdenum coil in the domed lower end of the zirconia tube. The volume around the wire and coil in the zirconia tube is filled with a powdered mixture of chrome and chrome oxide acting as the reference material. A second molybdenum wire is embedded in the lower end of the sleeve and acts as the thermal bath contact electrode. In so doing, both positive and negative electrodes of identical material are at equal temperature and parasitic thermocouple emf is eliminated. A bucking or null-balance voltage is applied across the sensor circuit to counter the potential developed by the oxygen ion transport between the molten steel and the reference chrome oxide. The magnitude of the voltage required to maintain oxygen ion equilibrium, or zero cell voltage, is used as the measure of oxygen content in the bath.

The above and still further objects, features and advantages of the present invention will become apparent upon considering the following detailed description of specific embodiments thereof, particularly when viewed in conjunction with the accompanying drawings.

DESCRIPTION OF THE PREFERRED EMBODIMENTS

Figure 1:
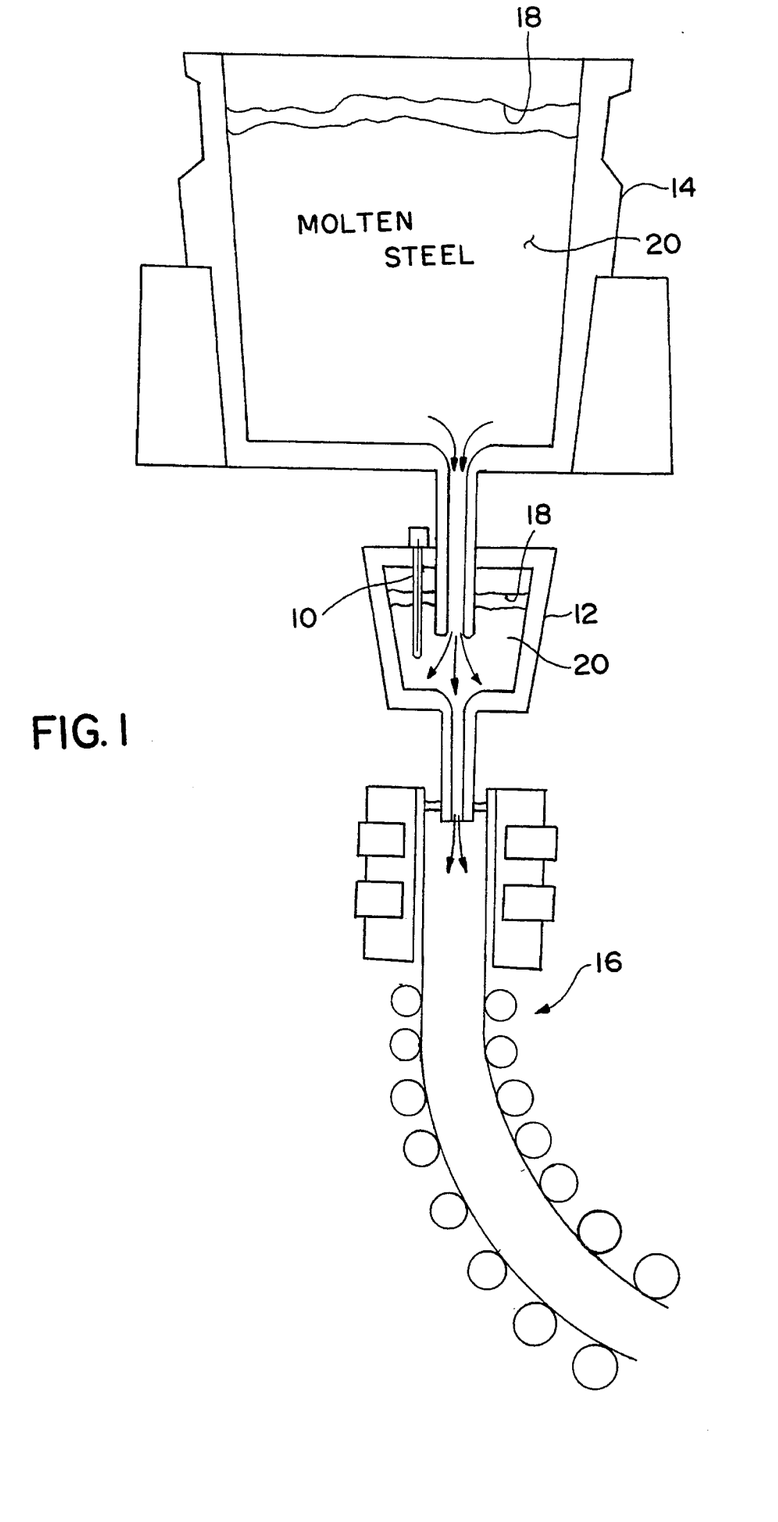
FIG. 1 is a diagram depicting a continuous casting process for molten steel.

For the purposes of clarity and consistency, all terms of spatial relationship in the following description assume the elongate axis of the oxygen sensor is vertically aligned with the penetrating or leading end extending downward into the container of molten steel as shown in FIG. 1. Hence the term "upper" refers to the direction toward the output end of the sensor and "lower" refers to the direction toward the measurement end of the sensor (i.e., immersion end).

A continuous oxygen content, sensor 10 according to the present invention is shown in FIG. 1 extending downward into a tundish or intermediate container 12 of molten steel located between a ladle 14 and a continuous casting machine 16. A layer of slag 18 is shown in the upper portion of the melt 20 in both the ladle and tundish.

Figure 2:
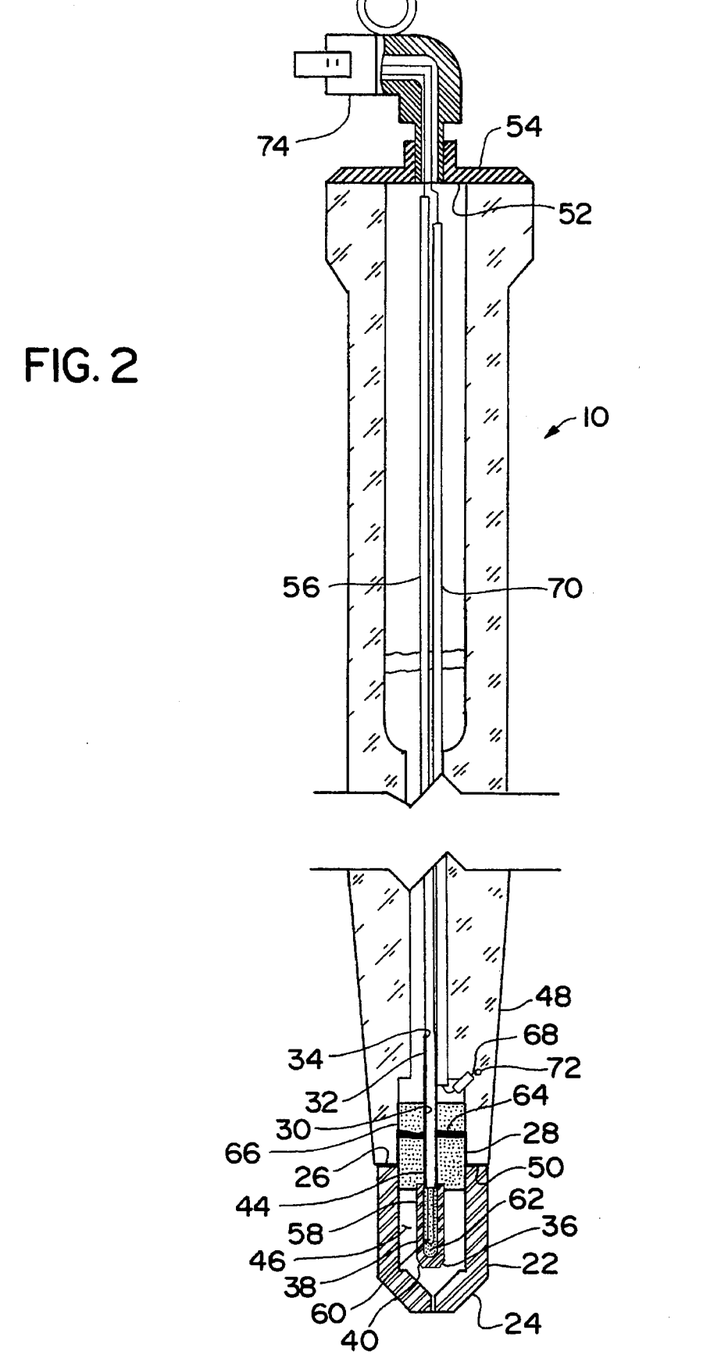
FIG. 2 is a broken side elevation in section of an oxygen sensor constructed in accordance with the present invention.
Figure 3:
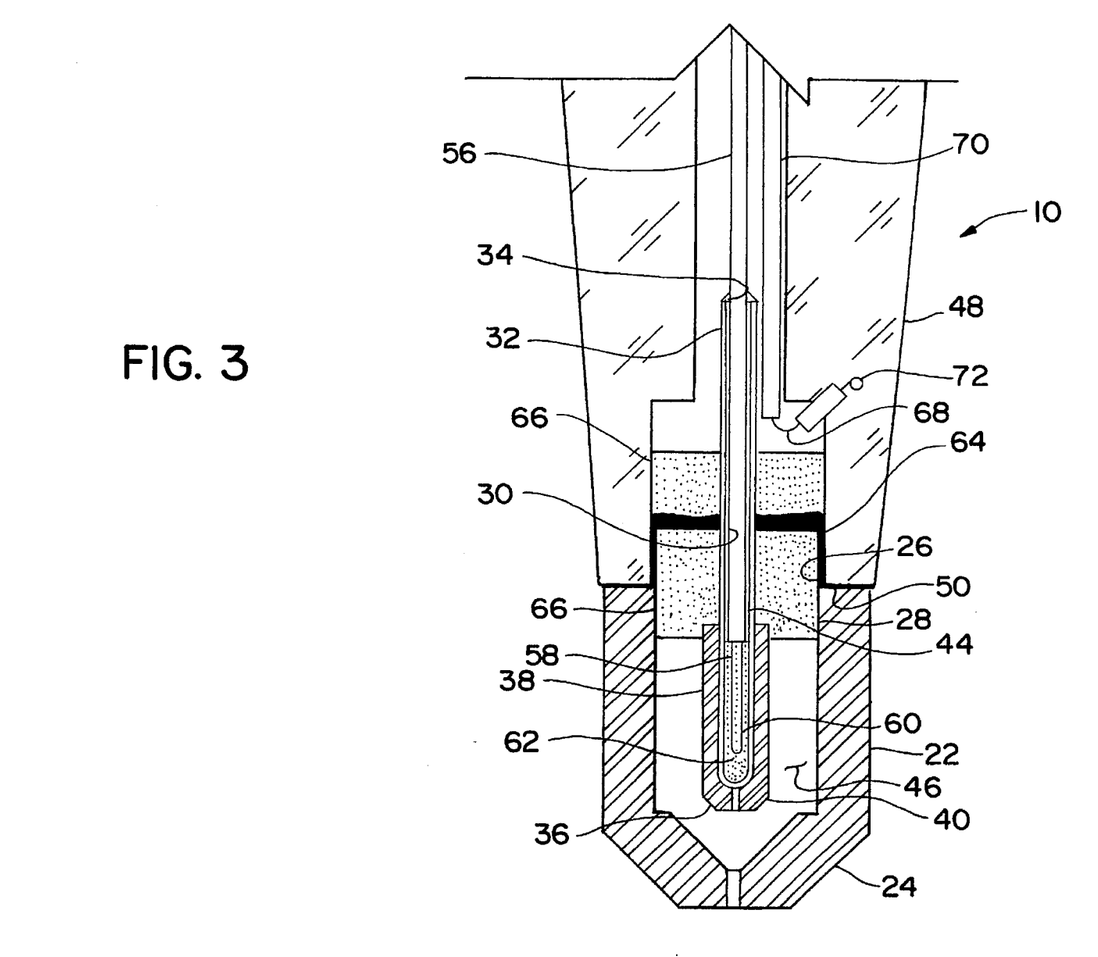
FIG. 3 is a side elevation view in section of the lower portion of an oxygen sensor according to the present invention.

The sensor, shown in FIG. 2, has a first ablative hollow shell 22, formed of, for instance, steel, at the downwardly extending end. Shell 22 has a closed dome-like lower end 24 and a flat open upper end 26. A lower alumina castable refractory collar 28 is disposed in tight adjacent fit with the upper portion of shell open upper end 26, and extends partially into the shell and partially above shell upper end 26. A central axial bore 30 is provided through lower collar 28 and a stabilized zirconia hollow tube 32 extends in tight fit through bore 30 from an open upper end 34 disposed above lower collar 28 to a closed dome-shaped lower end 36 disposed between the collar 28 and the shell lower end 24. A second ablative hollow shell 38 also formed of, for instance, steel, has a closed dome lower end 40 encasing the lower end 36 of zirconia tube 32 in tight adjacent fit, and extends upward to an open upper end 44 attached to lower collar 28. The second steel shell 38 is sized to provide an air gap 46 between first outer shell 22 and second inner shell 38.

A relatively thick-walled tubular elongate probe sleeve 48 made of an alumina-graphite composite has a flat open lower end 50 attached in surface contact to the open upper end 26 of outer ablative shell 22. Lower alumina castable refractory collar 28 extends upwardly in tight adjacent fit into the lower open end of probe sleeve 48. Collar 28 and sleeve 48 are formulated such that the coefficient of thermal expansion of collar 28 is equal or slightly higher than that of sleeve 48 to assure that a sealingly tight compression fit is maintained after immersion into the hot melt. Probe sleeve 48 extends upward to an open upper end 52 attached to a steel flange assembly 54. A first elongate insulator 56 extends downward from the upper end 52 of probe sleeve 48 axially through hollow zirconia tube 32 and lower collar 28 terminating within second steel shell 38 near shell open upper end 44. A first molybdenum wire 58 extends down through a bore in insulator 56 and forms a loop 60 extending downward into the closed dome lower end 40 of second shell 38. The volume enclosed by dome lower end 40 and surrounding loop 60 is packed with a chrome-chrome-oxide reference material 62.

A layer 64 of refractory cement is applied between the adjacent surfaces of probe sleeve 48 and first shell flat upper end 26 and between the inner surface of the probe sleeve and the outer surface of lower collar 28. Refractory cement layer 64 also extends across the upper surface of lower collar 28. An upper aluminum castable collar 66 is formed adjacent to and above cement layer 64 across the lower collar upper surface.

A second molybdenum wire 68 extends downward from flange assembly 54 in a second elongate insulator 70 and forms a loop 72 embedded in the alumina-graphite sleeve 48 near the sleeve lower end 50.

Wires 58 and 68 extend through flange assembly 54 to an external electrical connector 74 attached thereto.

In use, sensor 10 is inserted downwardly into the high temperature (2000°–3000° F.) liquid metal. Ablative outer shell 22 provides initial protection for the enclosed sensor components against the corrosive action of the slag layer forming the upper portion of the melt and elongate sleeve 48 supportingly extends the shell-enclosed sensor components deeply into the molten metal. After the slag layer has been penetrated, ablative outer shell 22 absorbs heat, extending the temperature rise time experienced by the inner shell 38 and enclosed reference material 62 and molybdenum wire loop 60 to combat thermal shock failure. As shell 22 ablates, heat conducted through the shell must then traverse the air gap 46 Until temperatures in the red-heat and above range are experienced by the inner surface of shell 22, air gap 46 provides a poor medium for thermal conductance and consequently helps delay thermal rise at the surface of inner shell 38. As such red-heat temperatures result in air-gap insensitive radiant transfer of heat, the inner shell 38 acts as a radiation shield to further control temperature rise time of the enclosed cell. As outer shell 22 dissolves, inner shell 38 further provides protection for the enclosed cell from molten metal intrusion. Inner shell 38 then dissolves exposing the now temperature equalized cell to the melt thus initiating the extended period of oxygen concentration measurement.

Oxygen ions migrate through the dense-fired zirconia tube wall creating an emf across the open circuit defined by the reference electrode loop 60 in the first molybdenum wire 58 embedded in chrome-chrome oxide reference material 62, and the counter electrode loop 72 in second molybdenum wire 68 embedded in the lower portion of the alumina-graphite sleeve 48 acting as the bath contact electrode. Embedding the counter electrode 72 in the lower portion of alumina-graphite sleeve 48 places the electrode in electrical contact with the metal bath due to the high electrical conductivity of the graphite material. Moreover, counter electrode or loop 72 achieves a temperature essentially equal to that imposed on reference electrode or loop 60. Finally, the extremely reducing environment provided by the oxygen gettering characteristic of the graphite permits the use of molybdenum wire that would otherwise vaporize in an even slightly oxygen-rich atmosphere. As a result, both electrodes are composed of molybdenum, relatively inexpensive in comparison to, for instance, platinum. Parasitic thermocouple effects are avoided without resort to complicating and costly compensation circuitry. The resulting signal is carried from the device through connector plug 74 to be processed along with independently obtained temperature measurements in accordance with the Nernst equation to provide a measure of fugacity or oxygen content in the bath of molten metal.

To overcome the problem of reference material oxygen depletion in a low oxygen concentration environment, or, conversely, reference material saturation in a high oxygen concentration environment, circuitry is included in the present invention taking advantage of the ability of the sensing electrolyte to function as an oxygen pump cell and actively pump oxygen ions through its solid lattice when an external voltage is applied across the two electrodes. A bucking or null-balance voltage is applied opposite the voltage developed by the oxygen potential, that is, the cell output voltage, or emf, developed between the reference electrode and the counter electrode is measured and a corrective counterbalancing potential is generated to fully reverse ion migration. With no net transfer of oxygen ions, reference material depletion is avoided.

Figure 4:
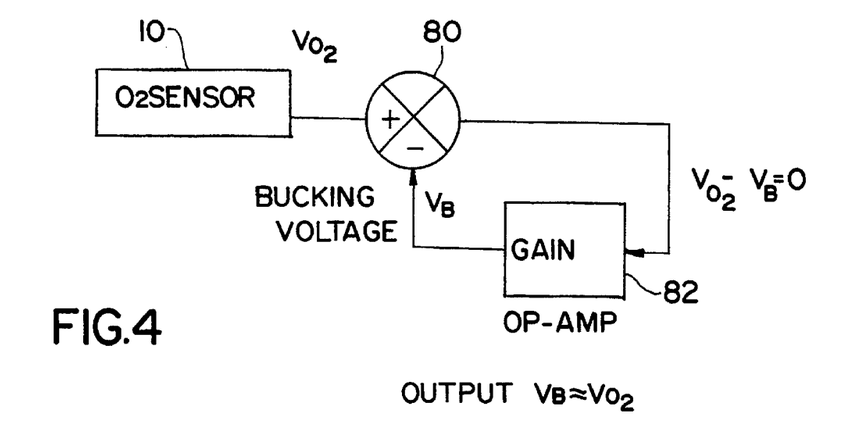
FIG. 4 is a circuit diagram showing a circuit for providing a continuous null-balance voltage to offset ion migration.

The cycle of measuring the charge produced by ion migration from the reference material and applying a replenishing countercharge, or bucking voltage, can be continuous or intermittent. In the continuous procedure, represented in block diagram form in FIG. 4, the output voltage of the cell 10 is continuously measured at a summing junction 80 and feedback loop voltage is generated as continuous output by an op-amp 82. The op-amp output required to thus maintain the constant net ion migration at zero is a measure of the continuous oxygen content of the melt.

Figure 5:
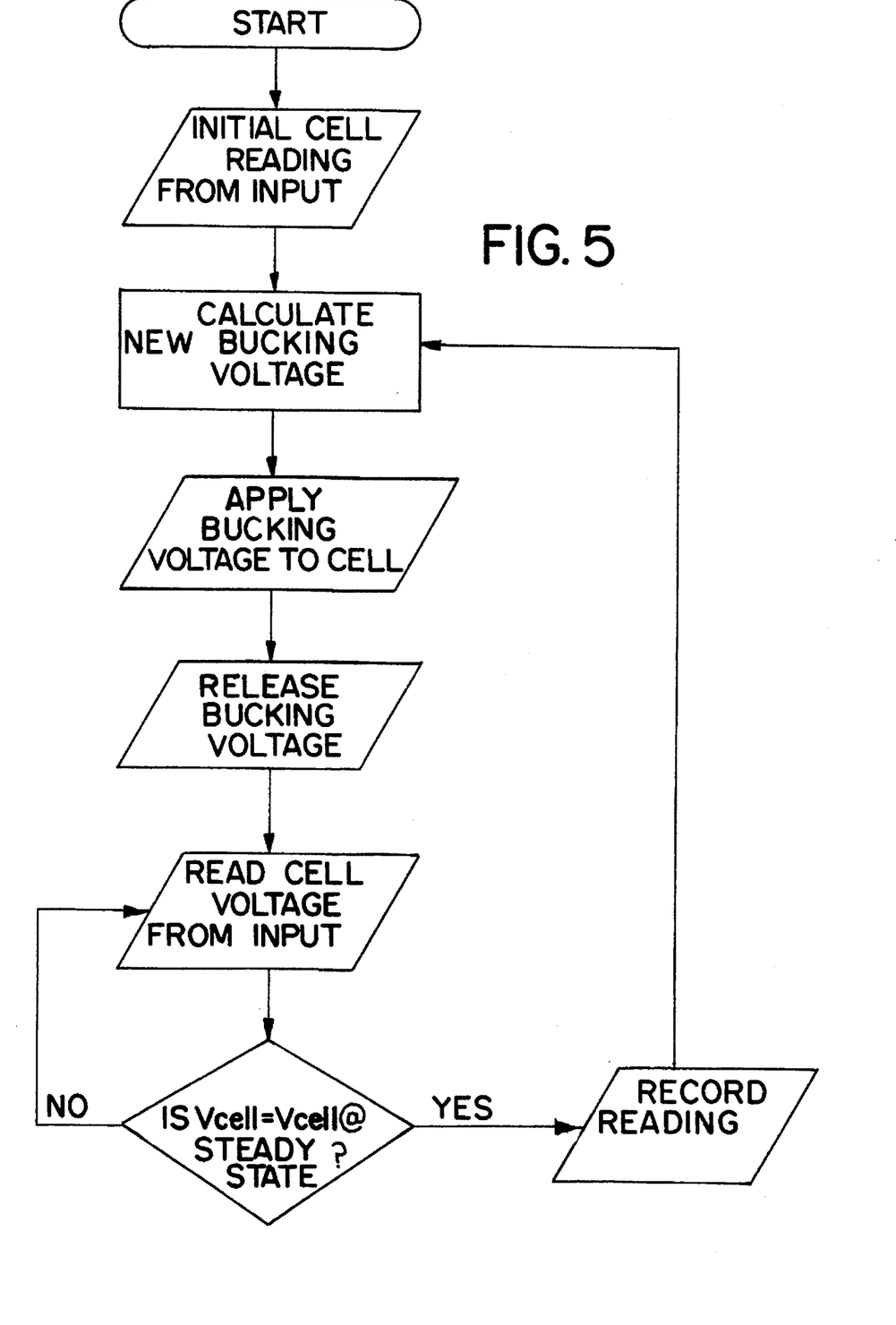
FIG. 5 is a flow chart of cyclic application of bucking or null-balancing voltage to an oxygen sensor.
Figure 6:
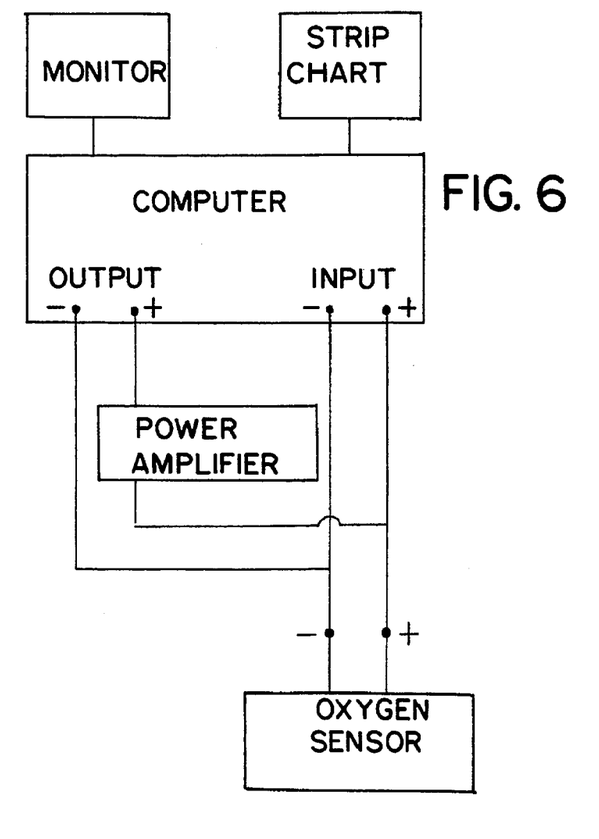
FIG. 6 is a block diagram of the monitoring and control functions of the oxygen sensor bucking voltage generator.

A periodic or cyclic implementation of the bucking voltage feature of the present invention, particularly well suited to extremely low partial pressure environments, is represented in flow diagram form in FIG. 5. The cycle starts with an initial reading of cell voltage that is input to a computer. This oxygen measurement data is processed by the computer to calculate a proper bucking voltage to saturate the reference material and to signal and control generation of this voltage by a power amplifier. Generally, a bucking voltage is selected to overdrive the cell slightly beyond the reference electrode material equilibrium position, that is, to actively transfer sufficient ions in a direction opposite natural diffusion to exceed the equilibrium state of the reference material. This voltage is applied to the cell and the cell emf is monitored and compared by the computer to the steady state signature of the cell. When steady state is re-established, then the next oxygen measurement is taken and a new cycle begins. The continuing oxygen measurements are fed from the computer to a monitor and/or strip chart, as represented in FIG. 6.

Figure 7:
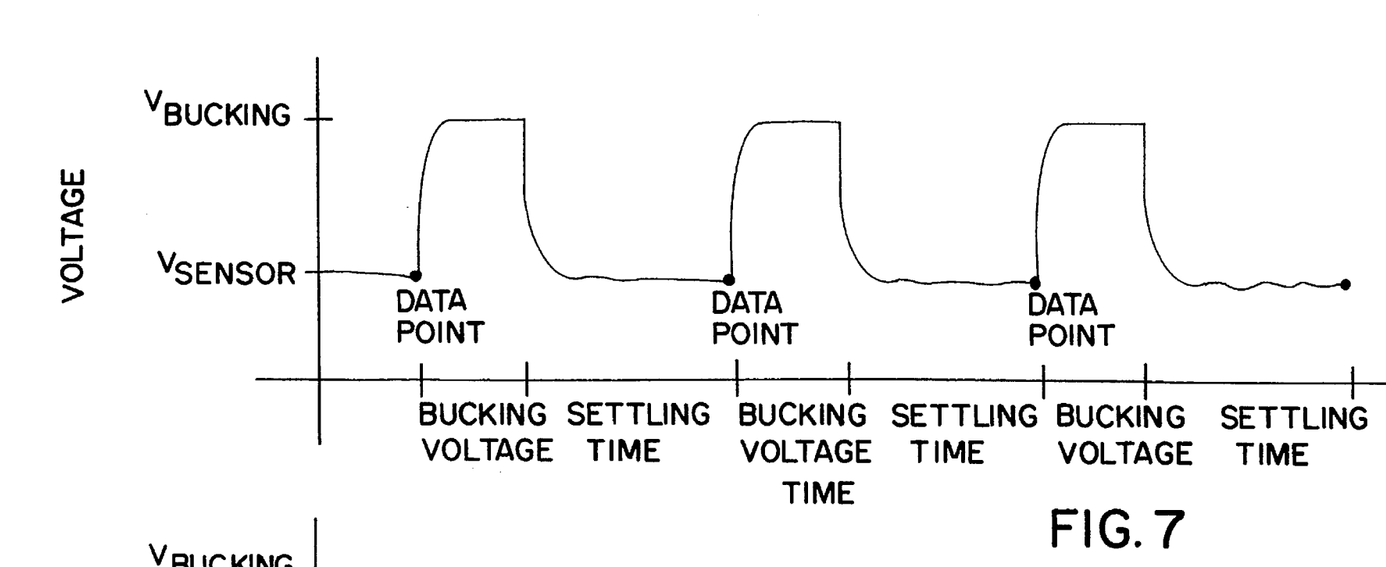
FIG. 7 is a plot of intermittent bucking voltage application as a function of time.

With each successive measurement of cell voltage output an application of an opposite voltage sufficient to overcharge the ion content of the reference material is triggered and the continuous cell output voltage is again monitored to discern when the electrochemical system of the sensor has once again reacquired a steady state condition, at which point the next cell voltage measurement is taken initiating a new cycle of the process, as illustrated in FIG. 7.

Figure 8:
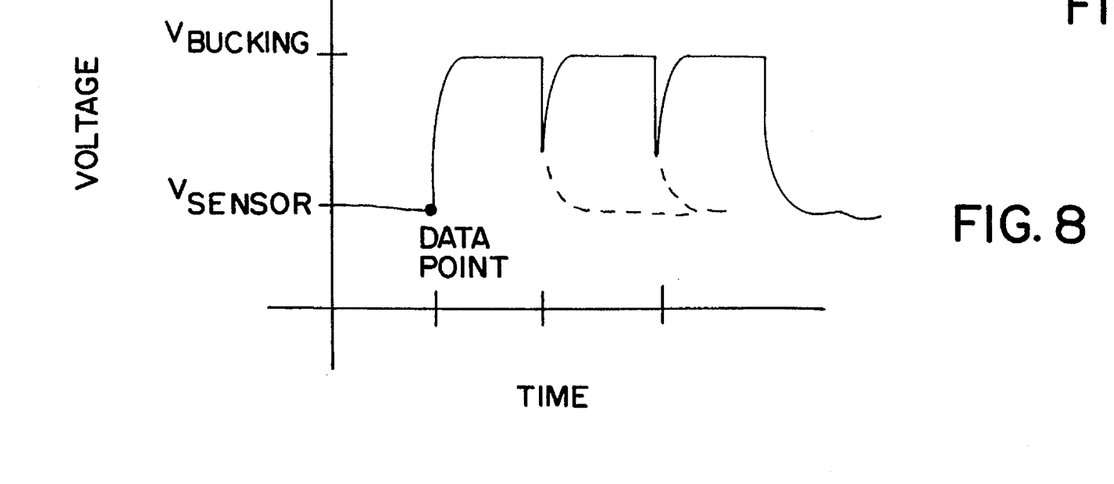
FIG. 8 is a plot of bucking voltage used with a first order regression calculation of an equilibrium data point.

Steady state output of the cell is achieved after the initial setup voltage decay, corresponding to the migration of saturated ions, has settled and a generally level or steady voltage is detected. The inflection of the voltage trace from steeply declining to near constancy can be identified and a suitable delay implemented before taking a voltage reading and applying a subsequent bucking voltage, as shown in FIG. 7. Alternatively, the initial sharp decay function can be sampled and a first order regression performed to predict a corresponding steady state voltage data point as shown in FIG. 8.

In addition, the two approaches can be combined to form a hybrid whereby regression estimated theoretical equilibrium data points are generated as a backup in the event that inflection and/or settling of the cell voltage to within pre-established predictive limits fails to occur.

The addition of the bucking circuit with oxygen pump all to the oxygen sensor provides a device generating an output proportional to oxygen content yet immune to oxygen-ion depletion or aggregation for long periods of continuous measurement.

Inasmuch as the present invention is subject to many variations, modifications and changes in detail, it is intended that the subject matter discussed above and shown in the accompanying drawings be interpreted as illustrative and not in a limiting sense.

What is claimed is:

1. An oxygen sensor having an electrochemical galvanic cell for continuous measurement of oxygen contaminant content in molten metal comprising:

an elongated electrically conductive composite sleeve having an axial through passage defined therein, an open upper end where said composite sleeve is capable of withstanding sustained thermal contact with said molten metal upon partial immersion and an open lower end;

a first hollow shell having an open upper end attached to said lower end of said sleeve, and a dome shaped closed lower end designed for immersion into and that establishes direct thermal and temporary contact with molten metal by said sensor;

a lower castable refractory collar having an upper surface and a lower surface, said collar extending in tight adjacent fit downwardly into said first shell and upwardly in tight adjacent fit into said sleeve lower end, said collar having an axial through-passage defined therein;

a second hollow shell having an open upper end axially attached to said lower surface of said collar and a closed lower end sized to extend downwardly into said first hollow shell dome-shaped lower end in spaced relationship therewith to form an air-gap spacing between said first and second hollow shells, said second hollow shell closed lower end being packed with a reference material of known oxygen content;

a hollow tube made of a material which enables oxygen ion migration through the walls thereof, said hollow tube having an open upper end and a closed lower end, said tube extending downward in tight adjacent fit through said collar axial through-passage and in tight adjacent fit within said second shell lower end;

a flange assembly attached across said upper open end of said sleeve, said flange assembly having an electrical connector plug attached thereto;

a first elongate insulator extending downward from said flange assembly through said sleeve, into tight adjacent fit through said hollow tube to a point slightly below said second shell upper end, said first insulator having a longitudinal borehole;

a first conductive wire extending from said plug through said flange assembly, downward through said borehole in said first insulator, into said hollow tube closed lower end, said first wire forming a first electrode loop within said closed lower end of said second hollow shell, which said first electrode loop is embedded in said reference material;

a second elongate insulator extending downward from said flange assembly through said sleeve to a point between said tube open upper end and said collar upper end, said second insulator having a longitudinal borehole; and a second conductive wire extending from said plug through said flange assembly, downward through said borehole in said second insulator, said second wire forming a second electrode loop embedded within said sleeve.

2. The oxygen sensor of claim 1 having an insulating air gap formed between said first shell dome-shaped lower end and said second hollow shell closed lower end.

3. The oxygen sensor of claim 1 further comprising an upper castable refractory collar formed in tight adjacent fit against said lower castable collar upper surface.

4. The oxygen sensor of claim 1 wherein said sleeve is formed of alumina-graphite.

5. The oxygen sensor of claim 1 wherein said first hollow shell is formed of ablative metal.

6. The oxygen sensor of claim 5 wherein said ablative metal is steel.

7. The oxygen sensor of claim 1 wherein said second hollow shell is formed of ablative metal.

8. The oxygen sensor of claim 7 wherein said ablative metal is steel.

9. The oxygen sensor of claim 1 wherein said reference material is a powdered mixture of chrome and chrome oxide.

10. The oxygen sensor of claim 1 wherein said hollow tube is formed of stabilized zirconia ceramic material.

11. The oxygen sensor of claim 1 wherein said first conductive wire is formed of molybdenum.

12. The oxygen sensor of claim 1 wherein said second conductive wire is formed of molybdenum.

13. The oxygen sensor of claim 1 wherein said lower castable refractory collar is formed of a material having a coefficient of thermal expansion equal to or slightly higher than the coefficient of thermal expansion of said elongate sleeve.

14. The oxygen sensor of claim 1 wherein said hollow tube is made from one of the chemically-doped ceramic group consisting of yttria-stabilized $ZrO_2$, MgO stabilized $ZrO_2$, CaO stabilized $ZrO_2$, $Y_2O_3$ stabilized thoria, and ceria stabilized $ThO_2$.

15. The oxygen sensor of claim 1 wherein said reference material is a mixture of nickel and nickel oxide.

16. The oxygen sensor of claim 1 wherein said reference material is a mixture of molybdenum and molybdenum oxide.

17. The oxygen sensor of claim 1 further comprising means for detecting the emf generated by the sensor and means for applying an equal but opposite counter emf across said electrodes to inhibit ion depletion of said reference material.

18. The oxygen sensor of claim 17 wherein said counter voltage is applied continuously across said electrodes.

19. The oxygen sensor of claim 17 wherein counter voltage is applied periodically across said electrodes.

20. The oxygen sensor of claim 19 wherein each application of counter voltage is controlled to actively transfer sufficient ions in a direction opposite natural diffusion to exceed the equilibrium state of said reference material.

21. The oxygen sensor of claim 20 wherein after each application of counter voltage, said reference material is permitted to reacquire equilibrium condition before subsequent applications of counter voltage.

22. In an electrochemical galvanic sensor cell for measuring the oxygen content of molten metal of the type in which the voltage produced by oxygen ion migration through a solid electrolyte material within said sensor, where said voltage is measured across an open sensor cell circuit connected between a reference material and the molten metal when said sensor cell with open circuit is immersed into said molten metal, the improvement comprising:

means for applying an equal but opposite bucking voltage across said cell circuit to prevent oxygen ion migration by maintaining a net ion migration current of zero and thereby to prevent reference material depletion or aggregation within said sensor cell; and     means to measure said applied bucking voltage as a measure of continuous oxygen content.

23. The method for measuring the oxygen content of molten metal comprising the steps of:

a) inserting a thermally hardened oxygen sensor having electrochemical galvanic cell construction into molten metal, said sensor capable of measuring the voltage produced by ionic transport of oxygen across a solid electrolyte material within said sensor, where said voltage is measured through an open circuit connected between a reference material and the molten metal;

b) applying a bucking voltage equal and opposite said measured sensor voltage to said circuit to maintain a net ion migration current of zero; and     c) calculating said molten metal oxygen content as a function of applied bucking voltage.

24. In an electrochemical galvanic sensor cell for measuring the oxygen content of molten metal of the type in which the voltage produced by oxygen ion migration through a solid electrolyte material within said sensor, where said voltage is measured across an open circuit connected between a reference material and the molten metal is measured when said sensor cell with open circuit is immersed in said molten metal, the improvement comprising:

means for intermittently applying oppositely directed bucking voltage across said cell circuit to produce reverse ion migration sufficient to saturate said reference material;

means to measure voltage decay across said circuit;

means to identify reacquisition of steady state ion migration current;

means to measure voltage produced by said steady state ion migration current;

means to calculate said molten metal oxygen content as a function of said measured voltage; and     means to initiate bucking voltage application after said voltage measurement.

25. In an electrochemical galvanic sensor cell for measuring the oxygen content of molten metal of the type in which the voltage produced by oxygen ion migration through a solid electrolyte material within said sensor, where said voltage is measured across an open circuit connected between a first electrode in contact with a reference material and a second electrode in contact with the molten metal when said sensor cell with open circuit is immersed into said molten metal and the circuit is electrically extended into said molten metal by an elongate supporting sleeve, the improvement comprising:

forming said elongate supporting sleeve of a highly electrically conductive material; and     embedding said second electrode in said conductive sleeve near said first electrode in electrical contact with said molten metal to avoid spurious thermal noise or parasitic thermocouple effects between said electrodes.

26. The improvement of claim 25 further comprising:

forming said conductive elongate sleeve of a highly oxygen-gettering material.

27. The improvement of claim 25 wherein said highly conductive sleeve material is alumina-graphite.

\* \* \* \* \*